US011976166B2

(12) United States Patent
Belowich et al.

(10) Patent No.: US 11,976,166 B2
(45) Date of Patent: May 7, 2024

(54) METHOD FOR PREPARING A BENZOPHENONE DERIVATIVE

(71) Applicants: Dow Global Technologies LLC, Midland, MI (US); Rohm and Haas Company, Collegeville, PA (US)

(72) Inventors: Matthew E. Belowich, Midland, MI (US); Alvin M. Maurice, Lansdale, PA (US); Mark D. Westmeyer, Collegeville, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 519 days.

(21) Appl. No.: 17/298,103

(22) PCT Filed: Dec. 2, 2019

(86) PCT No.: PCT/US2019/063914
§ 371 (c)(1),
(2) Date: May 28, 2021

(87) PCT Pub. No.: WO2020/131339
PCT Pub. Date: Jun. 25, 2020

(65) Prior Publication Data
US 2022/0033580 A1   Feb. 3, 2022

Related U.S. Application Data

(60) Provisional application No. 62/780,503, filed on Dec. 17, 2018.

(51) Int. Cl.
*C08G 65/22* (2006.01)
*C07C 45/64* (2006.01)
*C08G 65/26* (2006.01)

(52) U.S. Cl.
CPC .......... *C08G 65/2696* (2013.01); *C07C 45/64* (2013.01); *C08G 65/2612* (2013.01); *C08G 2650/24* (2013.01)

(58) Field of Classification Search
CPC .......................... C08G 65/22; C08G 18/3275
See application file for complete search history.

(56) References Cited

U.S. PATENT DOCUMENTS

| 4,602,097 A | 7/1986 | Curtis |
| 5,314,936 A | 5/1994 | Schwartz et al. |
| 2018/0134645 A1* | 5/2018 | Ossenbach ........... C07D 335/16 |

FOREIGN PATENT DOCUMENTS

| DE | 102006047863 | | 4/2007 |
| DE | WO 2017102675 | * | 6/2017 |
| EP | 3269764 | | 1/2018 |
| GB | 1193412 | * | 6/1970 |
| WO | 2010081749 | | 7/2010 |
| WO | 2011103878 | | 9/2011 |
| WO | 2016162389 | | 10/2016 |

* cited by examiner

*Primary Examiner* — Gregory Listvoyb
(74) *Attorney, Agent, or Firm* — Reid S. Willis

(57) ABSTRACT

The present invention is method comprising the steps of a) contacting 4-hydroxyphenone and a salt thereof with propylene oxide in a reactor heated to a temperature in the range of from 100° C. to 200° C. to form a poly(propylene oxide)-benzophenone intermediate; then b) contacting the intermediate with ethylene oxide in the heated reactor to form an alkoxylated benzophenone substituted with propylene oxide groups and ethylene oxide groups. The method of the present invention is useful for preparing a non-volatile alkoxylated benzophenone photoinitiator that gives long lasting gloss retention in an exterior architectural coating.

5 Claims, No Drawings

METHOD FOR PREPARING A BENZOPHENONE DERIVATIVE

BACKGROUND OF THE INVENTION

The present invention relates to a method for preparing a benzophenone derivative, more particularly a benzophenone functionalized with pendant propylene oxide and ethylene oxide repeat units.

Photoinitiators are used in exterior architectural coatings to improve dirt pickup resistance (DPUR) and gloss retention. Norrish type II photoinitiators are especially effective at improving these characteristics, presumably by crosslinking the surface of the polymer film. When excited by UV irradiation, the photoinitiator abstracts a hydrogen from the polymer, creating a reactive radical capable of crosslinking. It is also possible that the photoinitiator generates singlet oxygen via energy transfer to triplet oxygen. This singlet oxygen then reacts to form hydroperoxyl and hydroxyl radicals capable of inducing crosslinking via hydrogen abstraction from the polymer backbone.

Ideally, photoinitiators will improve targeted exterior performance without adversely impacting film flexibility and will have minimal impact on coating color either from the inherent absorption of the photoinitiator or its reaction byproducts. Benzophenone is an example of a photoinitiator that is especially effective for improving coating performance because it is capable of diffusing through the film to the surface before initiating the photo-induced crosslinking reaction. Crosslinking occurs primarily at the film surface because pigments in the coating absorb and/or screen UV light so the photoinitiator is primarily excited near the surface of the film.

Unfortunately, benzophenone has been determined to be a possible human carcinogen (IARC type 2B); moreover, benzophenone is considered a volatile organic compound (VOC) and is undesirable for its adverse environmental impact. This volatility has the additional disadvantage of causing variability in the crosslinking density of the film because benzophenone can evaporate from the film before reacting at the surface. The gloss retention performance of benzophenone is also known to rapidly decline after several months of exposure. Accordingly, it would be highly desirable to find a way to prepare a non-toxic and non-volatile photoinitiator that gives long lasting gloss retention in an exterior architectural coating.

SUMMARY OF THE INVENTION

The present invention addresses a need in the art by providing a method comprising the steps of a) contacting in the presence of a solvent 4-hydroxyphenone and a salt thereof with propylene oxide in a reactor heated to a temperature in the range of from 100° C. to 200° C. to form a poly(propylene oxide)-benzophenone intermediate; then b) contacting the intermediate with ethylene oxide in the heated reactor to form an alkoxylated benzophenone substituted with propylene oxide groups and ethylene oxide groups, wherein the mole:mole ratio of the benzophenone to the salt thereof is in the range of from 98:2 to 80:20; the mole:mole ratio of the propylene oxide to the benzophenone is in the range of from 1:1 to 20:1; and the mole:mole ratio of the ethylene oxide to the benzophenone is in the range of from 5:1 to 50:1.

The method of the present invention provides a way to make a non-volatile, non-toxic photoinitiator with excellent gloss retention in exterior architectural coatings.

DETAILED DESCRIPTION OF THE INVENTION

The present invention is a method comprising the steps of a) contacting in the presence of a solvent 4-hydroxyphenone and a salt thereof with propylene oxide in a reactor heated to a temperature in the range of from 100° C. to 200° C. to form a poly(propylene oxide)-benzophenone intermediate; then b) contacting the intermediate with ethylene oxide in the heated reactor to form an alkoxylated benzophenone substituted with propylene oxide groups and ethylene oxide groups, wherein the mole:mole ratio of the benzophenone to the salt thereof is in the range of from 98:2 to 80:20; the mole:mole ratio of the propylene oxide to the benzophenone is in the range of from 1:1 to 20:1; and the mole:mole ratio of the ethylene oxide to the benzophenone is in the range of from 5:1 to 50:1.

Propylene oxide and ethylene oxide groups are illustrated as follows:

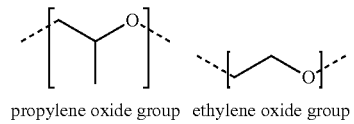

propylene oxide group  ethylene oxide group where the dotted line to the oxygen atom represents a point of attachment to a carbon atom or a terminal hydrogen atom, and the dotted line to the carbon atom represents a point of attachment to an oxygen atom. In accordance with the method of the present invention the propylene oxide groups are attached closest to the benzophenone group and that the ethylene oxide groups are attached to the propylene oxide groups, as illustrated in formula 1:

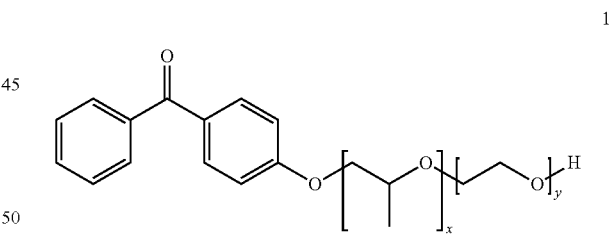

Preferably, x is from 2 to 13, more preferably to 10, and most preferably to 8; and y is preferably from 5, more preferably from 6, and most preferably from 10 to preferably 20, more preferably to 18, and most preferably to 16. Preferably, x+y is not greater than 25; preferably the number of ethylene oxide groups is greater than the number of propylene oxide groups; that is, preferably, y is greater x. The calculated Log P (cLog P) of the hydroxyl-terminated alkylene oxide group (R), as determined using ChemBioDraw Ultra 13.0 (PerkinElmer), which uses a chemical fragment algorithm method for assessing the partition coefficient of a molecule based on its constituent parts, is preferably in the range of from −4.0, more preferably from −3.5, and most preferably from −3.0, to −1.2, more preferably to −1.3, and most preferably to −1.5.

The functionalized benzophenone is advantageously prepared in two steps as follows: In a first step, 4-hydroxybenzophenone and a salt thereof are contacted with propylene oxide and a suitable solvent, preferably a high boiling polar aprotic solvent (b.p.>100° C.), in a pressure rated reactor. The mole:mole ratio of the 4-hydroxybenzophenone to the salt thereof is preferably in the range of 98:2, more preferably from 95:5, to 80:20. The salt is advantageously prepared in situ by addition of a strong base such as NaOH or KOH to the reactor. The mole:mole ratio of propylene oxide to 4-hydroxybenzophenone is preferably in the range of from 1:1, more preferably from 3:1, to 20:1, more preferably to 15:1, and most preferably to 10:1.

The reactor is heated to a temperature in the range of from 100° C., preferably from 120° C., to 200° C., preferably to 150° C. and the propylene oxide is added continuously, then held for a sufficient time to form the desired poly(propylene oxide)-benzophenone intermediate. In a second step, ethylene oxide is continuously added to the heated reactor, then held for a sufficient time to afford the desired product. The mole:mole ratio of the ethylene oxide to the 4-hydroxybenzophenone is preferably in the range of from 5:1, more preferably from 10:1 to 50:1, more preferably to 30:1, and most preferably to 25:1. The holding time for both the propylene oxide and ethylene oxide is preferably from 2 to 10 h. The reactor is then cooled and the high boiling polar aprotic solvent (e.g., dimethoxyethane) is removed to give the functionalized benzophenone. The final product is generally a mixture of products having a polydispersity ($M_w/M_n$) preferably in the range of from 1.2 to 3, more preferably to 2.

The functionalized benzophenone prepared by the process of the present invention is useful as a photoinitiator in coatings formulations.

EXAMPLES

General Alkoxylation Procedure:

A 9:1 mol:mol mixture of 4-hydroxybenzophenone and potassium 4-benzoylphenolate in dimethoxyethane (DME) was placed in a pressure-rated reactor having a capacity of 300 mL. The reactor was flushed with nitrogen and heated to 130° C. Propylene oxide (PO) was added continuously over a period of 30 min and then held at this temperature for 6 h. Ethylene oxide (EO) was then added to the reactor over a period of 30 min and held at this temperature for 6 h. The reactor was cooled to room temperature and vented. The solution was removed from the reactor and the solvent was removed in vacuo.

Example 1—Preparation of Benzophenone Derivative: x=5; y=11

Following the general alkoxylation procedure, the benzophenone derivative of FIG. 2, where x is 5 and y is 11, was prepared by addition of PO (10.7 mL, 153 mmol) and EO (19.1 mL, 383 mmol) to a solution of 4-hydroxybenzophenone (3.80 g, 19.2 mmol) and potassium 4-benzoylphenolate (0.45 g, 1.92 mmol) in DME (20 mL). After removal of the solvent in vacuo, 23.1 g (71%) of an oil was isolated.

Example 2—Preparation of Benzophenone Derivative: x=3; y=12

Following the general alkoxylation procedure, the benzophenone derivative of FIG. 2, where x is 3 and y is 12, was prepared by addition of PO (9.7 mL, 139 mmol) and EO (34.8 mL, 696 mmol) to a solution of 4-hydroxybenzophenone (6.90 g, 34.8 mmol) and potassium 4-benzoylphenolate (0.82 g, 3.48 mmol) in DME (35 mL). After removal of the solvent in vacuo, 42.8 g (85%) of an oil was isolated.

Example 3—Preparation of Benzophenone Derivative: x=6; y=6

Following the general alkoxylation procedure, the benzophenone derivative of FIG. 2, where x is 6 and y is 6, was prepared by addition of PO (23.7 mL, 339 mmol) and EO (21.2 mL, 424 mmol) to a solution of 4-hydroxybenzophenone (8.40 g, 42.4 mmol) and potassium 4-benzoylphenolate (1.00 g, 4.24 mmol) in DME (40 mL). After removal of the solvent in vacuo, 40.9 g (79%) of an oil was isolated.

Example 4—Preparation of Benzophenone Derivative: x=3; y=6

Following the general alkoxylation procedure, the benzophenone derivative of FIG. 2, where x is 3 and y is 6, was prepared by addition of PO (14.8 g, 212 mmol) and EO (26.5 mL, 530 mmol) to a solution of 4-hydroxybenzophenone (10.5 g, 53.0 mmol) and potassium 4-benzoylphenolate (1.25 g, 5.30 mmol) in DME (50 mL). After removal of the solvent in vacuo, 41.7 g (82%) of an oil was isolated.

Experimental surfactants were formulated into paints using the formulations in Table 1. Ingredients were added sequentially with continuous stirring using an overhead mixer. ECOSURF™ SA-9 is a non-reactive surfactant (Surfactant in Table 1) that was added to the comparative examples to keep the surfactant level constant. C1 and C2 refer to comparative Examples 1 and 2 respectively. C1 is the paint formulation without any photoinitiator and C2 is the formulation with benzophenone.

Defoamer refers to DOWSIL™ 8590 Defoamer; Microbicide refers to ROCIMA™ 63 Microbicide; Acrylic Binder refers to single stage polymer with the composition: 22 butyl acrylate/27 2-ethylhexyl acrylate/47.25 methyl methacrylate/2.5 methacrylic acid/1.25 ureido methacrylate, with a z-average particle size of 107 nm, a weight percent solids of 46.1% for the inventive examples and C1 (without benzophenone), and 45.3% for C2. BzP refers to benzophenone; Optifilm 400 refers to Optifilm Enhancer 400 Coalescent; RM-3000 refers to ACRYSOL™ RM-3000 Thickener; RM-8W refers to ACRYSOL™ RM-8W Thickener. BzP Ex1-BzP Ex4 refer to the benzophenone derivatives of Examples 1-4. DOWSIL, ROCIMA, ACRYSOL, and ECOSURF are all trademarks of The Dow Chemical Company or Its Affiliates.

TABLE 1

Paint Formulations

| | Paint Example # | | | | | |
|---|---|---|---|---|---|---|
| | 1 | 2 | 3 | 4 | C1 | C2 |
| Material | (g) | (g) | (g) | (g) | (g) | (g) |
| Water | 8.11 | 8.11 | 8.11 | 8.11 | 8.11 | 7.02 |
| Defoamer | 0.10 | 0.10 | 0.10 | 0.10 | 0.10 | 0.10 |
| Ti-Pure R-746 TiO$_2$ | 25.83 | 25.83 | 25.83 | 25.83 | 25.83 | 25.83 |
| Microbicide | 1.10 | 1.10 | 1.10 | 1.10 | 1.10 | 1.10 |
| Acrylic Binder | 64.26 | 64.26 | 64.26 | 64.26 | 64.26 | |
| Acrylic Binder w/BzP | | | | | | 65.36 |
| Optifilm 400 | 0.89 | 0.89 | 0.89 | 0.89 | 0.89 | 0.89 |

TABLE 1-continued

Paint Formulations

| Material | Paint Example # | | | | | |
|---|---|---|---|---|---|---|
| | 1 (g) | 2 (g) | 3 (g) | 4 (g) | C1 (g) | C2 (g) |
| RM-3000 | 1.05 | 1.05 | 1.05 | 1.05 | 1.05 | 1.05 |
| RM-8W | 0.35 | 0.35 | 0.35 | 0.35 | 0.35 | 0.35 |
| BzP Ex1 | 0.30 | | | | | |
| BzP Ex2 | | 0.30 | | | | |
| BzP Ex3 | | | 0.30 | | | |
| BzP Ex4 | | | | 0.30 | | |
| Surfactant | | | | | 0.30 | 0.30 |
| Total | 101.99 | 101.99 | 101.99 | 101.99 | 101.99 | 102.00 |

Gloss Retention Testing

Accelerated weathering was conducted using a QUV instrument (Q-Lab) according to ASTM-D 4587, Standard Practice for Fluorescent UV-Condensation Exposures of Paint and Related Coatings. Paint formulations were drawn down over chromate-treated aluminum panels with a 10 mil applicator and were dried in a controlled environment room (25° C., 50% RH) overnight. Panels were then placed outside (Collegeville, PA) facing South at a 45° angle for 6 d. After outdoor exposure, initial gloss measurements were made. The samples were placed into the QUV and exposed to a cycle consisting of 8 h of UV exposure (0.89 W/m², UVA lamp) at 60° C. followed by 4 h of a dark condensation period at 50° C. At the end of the 2000-h exposure, the final gloss measurements were made on the samples. Gloss was measured using a BYK Gardner micro-TRI-gloss meter. Table 2 illustrates the Δ60° Gloss after 2006 h of exposure.

TABLE 2

Δ60° Gloss After 2006 h Exposure

| Paint # | Δ60° Gloss |
|---|---|
| 1 | −18.7 |
| 2 | −26.7 |
| 3 | −38.9 |
| 4 | −31.1 |
| C1 | −50.7 |
| C2 | −47.5 |

The data show that the paint formulations containing the benzophenone derivative prepared by the process of the present invention exhibits a markedly lower drift in 460° gloss as compared with the formulations that contain benzophenone or no photoinitiator. Though not bound by theory it is believed that the observed improved gloss retention observed for the benzophenone derivatives over benzophenone may derive from differences in distribution and stability within the film. Benzophenone, being relatively volatile, will more readily migrate through the film and either react or evaporate prematurely from the paint surface, leading to superficial crosslinking of the paint film. In contrast, the inventive benzophenone derivatives are not volatile and therefore cannot evaporate from the film. As the paint surface wears away, the availability of additional photoinitiator for polymer crosslinking leads to improved gloss retention.

It is further believed that the effectiveness of the invention is derived from the surface active nature of the compounds; the combination of hydrophobe (benzophenone) and hydrophile (PO-EO oligomer) will cause the compound to migrate to latex/water or water/air interfaces; after drying, the photoinitiator may be preferentially located at the film surface. However, excess surfactant in a formulation can cause water resistance issues such as blistering or swelling. By varying the PO (less hydrophilic) and EO (more hydrophilic) groups of the derivatives, the water sensitivity and gloss retention performance of the paint formulation can be tuned.

The invention claimed is:

1. A method comprising the steps of a) contacting in the presence of a solvent 4-hydroxyphenone and a salt thereof with propylene oxide in a reactor heated to a temperature in the range of from 100° C. to 200° C. to form a poly (propylene oxide)-benzophenone intermediate; then b) contacting the intermediate with ethylene oxide in the heated reactor to form an alkoxylated benzophenone substituted with propylene oxide groups and ethylene oxide groups, wherein the mole:mole ratio of the benzophenone to the salt thereof is in the range of from 98:2 to 80:20; the mole:mole ratio of the propylene oxide to the benzophenone is in the range of 1:1 to 20:1; and the mole:mole ratio of the ethylene oxide to the benzophenone is in the range of from 5:1 to 50:1.

2. The method of claim 1 wherein the solvent is a polar aprotic solvent having a boiling point >100° C., wherein the reactor is a pressure rated reactor.

3. The method of claim 2 wherein mole:mole ratio of the benzophenone to the salt thereof is in the range of from 95:5 to 80:2; the mole:mole ratio of the propylene oxide to the benzophenone is in the range of from 3:1 to 10:1; and the mole:mole ratio of the ethylene oxide to the benzophenone is in the range of from 10:1 to 25:1.

4. The method of claim 3 wherein the alkoxylated benzophenone is represented by formula 1:

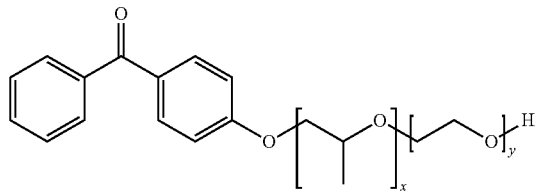

1 where x is from 2 to 13 and y is from 5 to 20 with the proviso that x+y is not greater than 25.

5. The method of claim 4 wherein y is greater than x.

* * * * *